United States Patent [19]

Feuerborn et al.

[11] Patent Number: 5,591,133
[45] Date of Patent: Jan. 7, 1997

[54] FLEXING SAFETY SHIELD FOR HYPODERMIC NEEDLES

[75] Inventors: Art Feuerborn; David Feuerborn, both of Camarilllo, Calif.

[73] Assignee: Lawrence R. Koh, Los Angeles, Calif.

[21] Appl. No.: 257,352

[22] Filed: Jun. 9, 1994

[51] Int. Cl.$^6$ ..................................................... A61M 5/32
[52] U.S. Cl. ........................... 604/192; 604/198; 604/263
[58] Field of Search .................................... 604/198, 192, 604/187, 263, 110

[56] References Cited

U.S. PATENT DOCUMENTS

| | | |
|---|---|---|
| 1,373,669 | 4/1921 | Pittenger . |
| 2,571,653 | 10/1951 | Bastien . |
| 2,894,509 | 7/1959 | Bednarz . |
| 3,536,073 | 10/1970 | Farb . |
| 3,780,734 | 12/1973 | Wulff . |
| 3,884,230 | 5/1975 | Wulff . |
| 3,889,673 | 6/1975 | Dovey et al. . |
| 3,905,375 | 9/1975 | Toyama . |
| 4,139,009 | 2/1979 | Alvarez . |
| 4,170,993 | 10/1979 | Alvarez . |
| 4,232,669 | 11/1980 | Nitshke . |
| 4,266,543 | 5/1981 | Blum . |
| 4,356,822 | 11/1982 | Winstead-Hall . |
| 4,425,120 | 1/1984 | Sampson et al. . |
| 4,430,080 | 2/1984 | Pasquini et al. . |
| 4,559,043 | 12/1985 | Whitehouse et al. . |
| 4,573,976 | 3/1986 | Sampson et al. . |
| 4,592,744 | 6/1986 | Jagger et al. . |
| 4,631,057 | 12/1986 | Mitchell . |
| 4,643,199 | 2/1987 | Jennings, Jr. et al. . |
| 4,659,330 | 4/1987 | Nelson et al. . |
| 4,664,259 | 5/1987 | Landis . |
| 4,675,005 | 6/1987 | DeLuccia . |
| 4,676,783 | 6/1987 | Jagger et al. . |
| 4,681,567 | 7/1987 | Masters et al. . |
| 4,702,739 | 10/1987 | Milorad . |
| 4,731,059 | 3/1988 | Wanderer et al. . |
| 4,867,172 | 9/1989 | Haber et al. ......................... 604/263 X |
| 4,898,589 | 2/1990 | Dolgin et al. ........................... 604/198 |
| 4,915,697 | 4/1990 | DuPont . |

(List continued on next page.)

OTHER PUBLICATIONS

"Invention Reduces Needle Prick Risk," Insight, Apr. 23, 1990.
"Needle Designs Seek to Limit Disease Spread," The Cutting Edge, The Washington Post, Jun. 23, 1987.
"Needle Guard Reduces Needlesticks," Design News, Oct. 23, 1989.
"One-time throwaway," Popular Science, vol. 235, Jul. 1989.
"Safety–Ject Reduces Risk to Medical Profession of Accidental Contamination By Needles," Bette Gedde, Safety–Ject Medical Products, Inc., Barron's, Dec. 18, 1989.
"A Syringe to Prevent Accidental Needle Sticks," Edmund L. Andrews, The New York Times, Apr. 28, 1990.
"Pen Makes Injections Easier for Diabetics," Wall Street Journal, Jul. 10, 1990.
"The Engineer's Role on Halting AIDS," Technology Review, Oct. 22, 1988.

*Primary Examiner*—John D. Yasko
*Attorney, Agent, or Firm*—Gene W. Arant

[57] ABSTRACT

A shield for hypodermic needles is disclosed which is preferably of unitary construction and made of a plastic such as polypropylene. The shield is preferably cylindrical and is formed as a sleeve with a hollow bore for receiving the cannula of a hypodermic needle assembly. The shield is fixed at the hub of the needle assembly and can be either attached to the hub using a method such as heat or sonic sealing, or it can be manufactured with the hub as a unit. The sleeve has an upper axially rigid portion toward the tip end of the cannula, a lower axially rigid portion at the hub end, and at least two displaceable portions between the upper and lower rigid portions. Each of the displaceable portions are further subdivided into at least two subportions by introducing slits into the displaceable portions. The sleeve has hinging portions at the interfaces between the rigid portions and the displaceable portions, and a hinging portion at the interface between the displaceable portions.

3 Claims, 8 Drawing Sheets

U.S. PATENT DOCUMENTS

| | | |
|---|---|---|
| 4,917,672 | 4/1990 | Terndrup et al. . |
| 4,935,012 | 6/1990 | Magre et al. . |
| 4,935,013 | 6/1990 | Haber et al. ............... 604/198 X |
| 4,994,045 | 2/1991 | Ranford . |
| 4,997,422 | 3/1991 | Chow et al. . |
| 4,998,922 | 3/1991 | Kuracina et al. . |
| 5,000,167 | 3/1991 | Sunderland . |
| 5,067,490 | 11/1991 | Haber . |
| 5,135,510 | 8/1992 | Maszkiewicz et al. . |
| 5,181,524 | 1/1993 | Wanderer et al. . |
| 5,184,721 | 2/1993 | Wengyn et al. . |
| 5,269,765 | 12/1993 | Kuracina ..................... 604/192 |

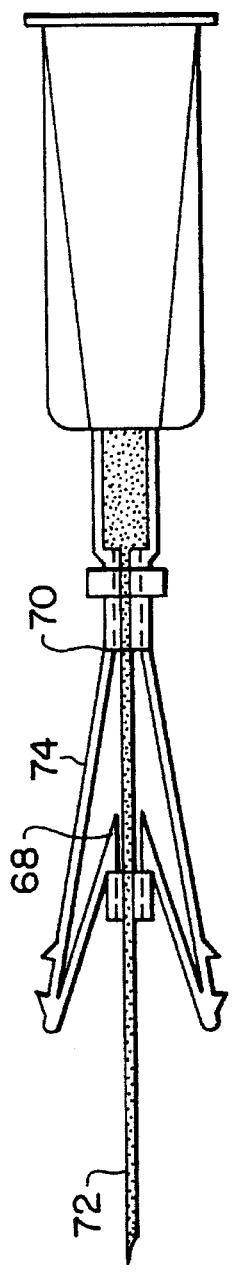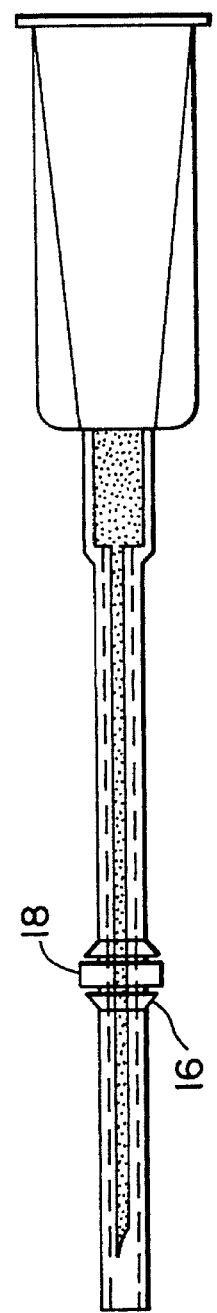
FIG. 8
FIG. 9

FLEXING SAFETY SHIELD FOR HYPODERMIC NEEDLES

BACKGROUND OF THE INVENTION

1. Field of the Invention

The apparatus of the present invention relates to hypodermic needles, and more particularly to a shield for hypodermic needles to protect medical personnel and others from accidental contact with needles that may have been exposed to contagious and/or blood-borne diseases.

2. Art Background

Hypodermic needles are indispensable to the health care industry for both drawing bodily fluids from and administering medication to patients. Most hypodermic needles currently in use are disposed of, after one use, in a waste receptacle to limit further contact between medical personnel or patients and the cannulas of the used needles. Avoiding contact with used needles is essential to prevent the transmission of diseases, particularly blood-borne diseases such as acquired immune deficiency syndrome (AIDS). Although medical personnel are trained to handle used needles with extreme care to avoid exposing themselves, the large volume of unshielded syringes renders such accidental exposure commonplace.

The hypodermic syringes now commonly in use offer insufficient protection against accidental contact with their cannulas after use. The most common hypodermic needle includes a replaceable plastic cap to cover its cannula. The cap is removed just prior to use and is replaced thereafter. The act of replacing the cap exposes medical personnel to the danger of accidental contact, particularly subcutaneous contact, with the used cannula. Moreover, the person administering the needle may forget to replace the cap, or may do so incorrectly, thus increasing the probability of accidental contact between the used cannula and those who must handle medical refuse.

The designs of hypodermic needles now commonly in use also do little to discourage re-use of the needle. In recent years, it has become common for certain persons such as intravenous drug users to illegally use needles discarded by hospitals, clinics and other legitimate users. This illegal use further increases the spread of communicable diseases such as AIDS. The user of discarded needles of current designs must only remove the needle's plastic cap to access the dirty cannula.

A number of prior art needle shields have been developed in an attempt to solve the problems of accidental exposure and illicit re-use. Many of these devices create a "safe" position with a cylindrical outer sleeve that radially surrounds the cannula such that the cannula is not exposed after use. Many of these designs, however, require that the needle administrator take an affirmative act to place the device in the safe position. This is a feature of U.S. Pat. Nos. 5,067,490, 4,935,010, 4,997,422, 5,000,167 and 5,181,524.

These devices suffer from problems similar to those of the common hypodermic needle using a plastic cap. The act of placing the device in the safe position exposes the needle administrator to the danger of accidental contact with the cannula. Moreover, the needle administrator may forget to place the device in the safe position and thus fail to reduce the probability of accidental contact between the cannula and refuse handlers.

Other prior art designs have been developed in an attempt to provide a needle shield that automatically resets to a safe position after the needle is used, thus eliminating the need for an affirmative act by the administrator. These devices also typically employ a sleeve to axially surround the cannula. The cannula is coupled to a spring such that when an axial force of sufficient magnitude is applied by the needle administrator to the syringe, the cannula protrudes from the sleeve to permit injection. The spring develops a reactive axial force in the direction opposite to the applied force. When the administrator releases the axial force as the needle is withdrawn, the spring forces the cannula to retract within the sleeve. This technique is disclosed in U.S. Pat. Nos. 4,917,672, 5,135,510 and 4,915,697. The '697 patent employs a plastic pleating as a spring. The '672 patent discloses a spring fitted around a cannula and a sleeve that is fitted on top of the spring. For this design, the sleeve obscures the cannula and thus makes it more difficult for needle administrators to apply the cannula to a particular point.

The use of a spring to reset the cannula into the safe position suffers from a major drawback. If the spring is chosen with a relatively low spring constant, a very small force, not substantially greater than the force required to cause subcutaneous contact with an unshielded needle, will allow the cannula to protrude from the sleeve. Thus, if a needle administrator accidently provides a small amount of axial force, the cannula can be accidentally exposed. Conversely, if a spring is chosen with a relatively high spring constant, so that significant axial force is required to expose the cannula, the spring will create a resistance that increases as the cannula protrudes further from the sleeve; the reactive force created by a spring increases as the length of the spring is decreased through compression. Thus, to attain an appropriate depth of insertion in the patient, the needle administrator must apply an increasingly greater force than was required to initially disengage the needle from the safe position. This increasing force will be transmitted to the patient, causing discomfort, and will likely render smooth administration of an injection difficult. This inherent property of springs therefore makes it difficult to solve the problems of inadvertent exposure and unacceptably large resistance during the injection process.

Thus, there is much room for improvement in the art of shielding the handles of hypodermic needles from the cannulas of those needles after they have been used.

SUMMARY OF THE INVENTION

The shield of the present invention is a novel and non-obvious improvement over previous attempts to shield handlers of hypodermic needles from accidental contact with such needles once they are used. The present invention provides a sleeve which is initially configured in a "safe" position. The safe position occurs when the cannula is completely withdrawn inside of the sleeve so that no part of the cannula protrudes from the sleeve. The sleeve's structural characteristics are such that an initial threshold of axial force must be exceeded before the sleeve's initial rigidity is overcome, thereby permitting exposure of the cannula. This threshold of force can be optimized by varying the structural characteristics of the sleeve (i.e. materials of composition, thickness, diameter, etc.) such that the threshold force is significantly greater than the axial forces typical of those that create accidental subcutaneous contact of unshielded needles. At the same time, the threshold force is not so great as to interfere with smooth initial insertion of the cannula during an intended use.

Moreover, once the threshold force is exceeded, the amount of force necessary to further displace the shield of the present invention to expose the cannula to the extent necessary to achieve an appropriate depth within a patient is not substantially greater than (if not less than or equal to) the threshold force, so as to not interfere with the smooth administration of an injection. This is accomplished by forming displaceable portions of the sleeve that hinge at predetermined locations to facilitate their displacement. The threshold axial force is that force necessarily applied to the syringe, with the sleeve against the surface to be penetrated, to overcome the initial rigidity of the sleeve and thereby cause the displaceable portions to hinge at the predetermined locations. Once hinging begins, the force necessary for continued displacement of the displaceable portions (and thus further exposure of the cannula) can actually be less (but not substantially greater) than the threshold force required to initiate hinging.

During withdrawal of the needle, the elasticity of the sleeve causes the displaceable portions of the sleeve to retract until the sleeve has once again returned to its initially rigid state and the cannula has become completely withdrawn inside of the sleeve. Once again, application of the threshold axial force is necessary to re-expose the cannula. Thus, the shield automatically returns to its "safe" state.

Finally, a locking feature is provided which can be engaged while the shield is in the safe position. A sliding collar is provided that is slidably engaged within a collar index using a force in a direction opposite to that required to expose the cannula. Thus, the locking mechanism is engaged while the shield is already providing protection via the safe position and in a manner which should not create a threshold axial force. Even if the administrator forgets to engage the locking mechanism, the shield still provides protection to handlers as long as forces exerted on the shield do not exceed the threshold axial force. The collar index is designed to permit stretching of the collar such that the collar can be slipped over the border forming the index to engage the index. Once engaged, the collar snaps back to its original diameter and cannot be disengaged from the index. In this "locked" state, a force which greatly exceeds the threshold force of the "safe" position is required to expose the cannula because the collar prohibits displacement of the displaceable portions of the sleeve. Further, it discourages illicit use of the discarded needle by making exposure of the cannula extremely difficult.

It is therefore an objective of the present invention to provide a hypodermic needle shield which requires a threshold axial force, to go from a safe position to an exposed position, that is significantly greater than axial forces typically encountered during most unintentional subcutaneous exposures to used cannulas, but is not so great as to cause abnormal discomfort to a patient during initial insertion.

It is further an objective of the present invention to provide a hypodermic needle shield that, once the threshold force has been exceeded, the force necessary for continued displacement of the shield is less than that which would cause disruptive interference with the injection process.

It is still further an objective of the present invention to provide a hypodermic needle shield which when withdrawn from the patient returns immediately to the safe position.

It is still further an objective of the present invention to provide a hypodermic needle shield which is comprised of a material configured to provide the desired mechanical characteristics while being inexpensive and simple to manufacture, and adaptable to any currently available hypodermic needle assembly.

It is still further an objective of the present invention to provide a hypodermic needle shield which has a locking feature that discourages illicit use after disposal and greatly increases the force necessary to overcome the safe position and to expose a used cannula.

These and other objectives of the present invention will become apparent in light of the following detailed description.

BRIEF DESCRIPTION OF THE DRAWINGS

FIG. 8 illustrates another alternate embodiment of the sleeve of the present invention in an open position.

FIG. 9 illustrates the shield of the present invention in a safe and locked position.

DETAILED DESCRIPTION OF THE INVENTION

Figure 1:
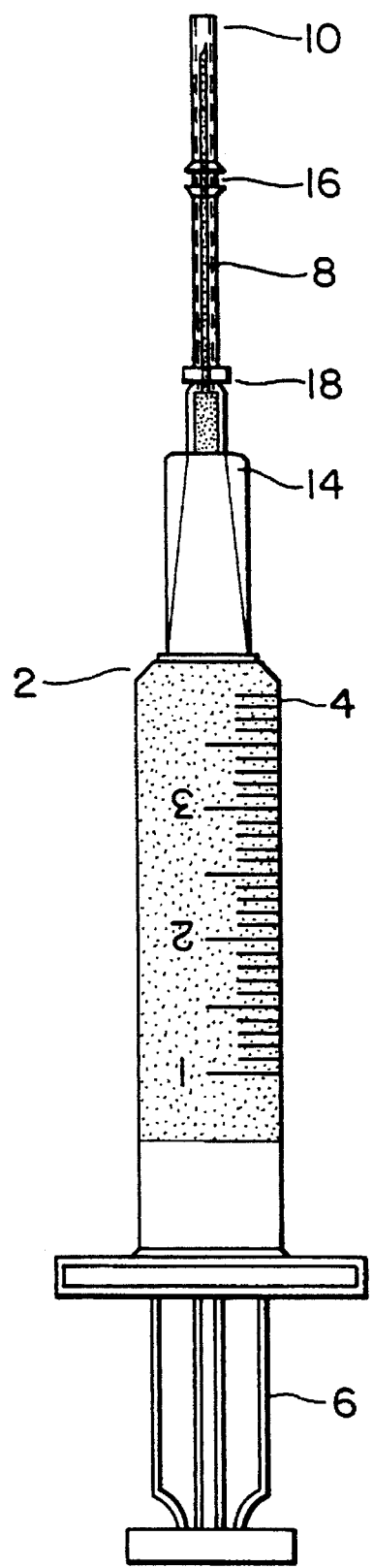
FIG. 1 illustrates a hypodermic needle in conjunction with the needle shield of the present invention.

FIG. 1 illustrates a hypodermic needle assembly 2 in conjunction with the needle shield of the present invention. As shown in FIG. 1, the hypodermic needle assembly 2 includes a syringe barrel 4 housing a portion of a plunger 6. The barrel 4 is coupled to a hub 14 which is coupled to a cannula 8. As shown in FIG. 1, the needle shield of the present invention includes a cylindrical sleeve 10 which is coupled to the hub 14.

The sleeve 10 may include a thin membrane at the tip of the sleeve toward the tip end of cannula 8. The membrane would be broken as the cannula 8 protrudes from sleeve 10, such as during insertion into a patient or vial. The membrane can serve several purposes, including hermetically sealing the cannula until a first use. The membrane can also be used to contribute towards the initial threshold force necessary to cause exposure of the cannula. Even after the membrane has been initially pierced, it can continue to provide resistance to axial displacement of the sleeve, thereby contributing towards the requisite threshold force.

The cylindrical sleeve 10 may be coupled to a hub 14 of any size or shape. Further, the sleeve 10 could be manufactured with the hub 14 as one piece. Thus, the needle shield of the present invention may be manufactured to operate with any existing line of hypodermic needles, or it could be customized for integrated manufacture. The manufacturer also has the option to retain the existing overcap and packaging for the needle.

In the preferred embodiment, the sleeve 10 is made from POLYPROPYLENE. The sleeve may also be made of HDPE, LDPE, DELRIN, NYLON or any materials providing the desired mechanical characteristics as disclosed herein.

Figure 2:
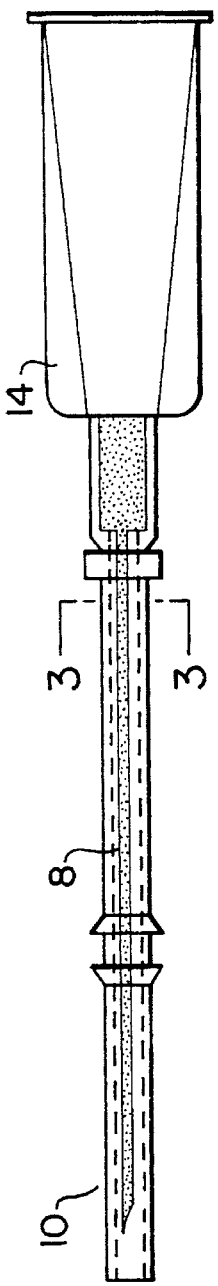
FIG. 2 illustrates the needle shield of the preferred embodiment of the present invention in the safe position.
Figure 3:
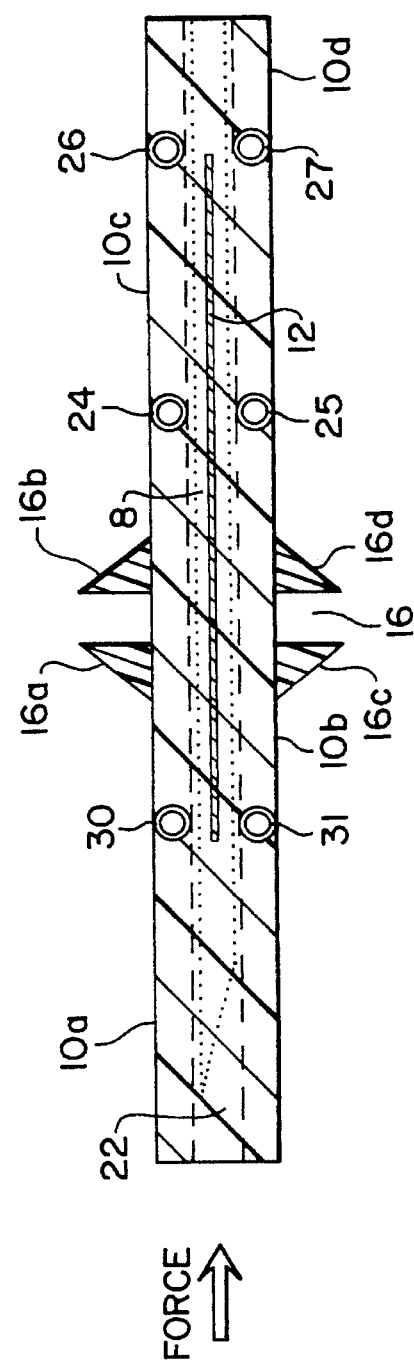
FIG. 3 illustrates an exploded longitudinal cross sectional view along lines A—A of FIG. 2.

FIG. 2 illustrates the needle shield of the present invention. As illustrated in FIG. 2, when the needle shield is in the safe position, the cannula 8 is completely housed within the cylindrical sleeve 10. FIG. 3 illustrates a longitudinal cross-sectional view taken along lines A—A of FIG. 2. The cylindrical sleeve 10 is preferably a unitary plastic member that defines an axially extending central bore 22 to slidably receive the cannula 8. The cylindrical sleeve 10 includes a radially rigid upper portion 10a which is at least coextensive with the tip of the cannula when the shield is in the safe position, a radially rigid lower portion 10d, and displaceable portions 10b and 10c. Displaceable portions 10b and 10c each have at least two subportions. Each of the subportions of displaceable portions 10b and 10c are hinged by hinging portions 24, 25 respectively. Each of the subportions of displaceable portion 10b are hinged at their interface with radially rigid upper portion 10a by hinging portions 26, 27. Each of the subportions of displaceable portion 10c are integrally hinged at their interface with lower radially rigid portion 10d by hinging portions 30, 31.

In the preferred embodiment, the subportions of displaceable portions 10b and 10c are formed by creating two slits 12 along the length of the cylindrical sleeve 10 between radially rigid upper and lower portions 10a and 10d. The slits 12 are preferably separated by 180 degrees around the sleeve 10. The slits 12 may completely sever the cylindrical sleeve 10, or may be formed such that a thin layer of plastic remains along the length of the slit. It will be appreciated by those of skill in the art that more than two slits may be formed in sleeve 10 and that the slits may be arranged at various angles around the sleeve 10 to attain the desired initial rigidity characteristics of the sleeve 10, as well as the desired force vs. displacement response of the sleeve once the threshold has been exceeded. The number of slits will of course govern the number of subportions making up each displaceable portion 10b and 10c.

Figure 4:
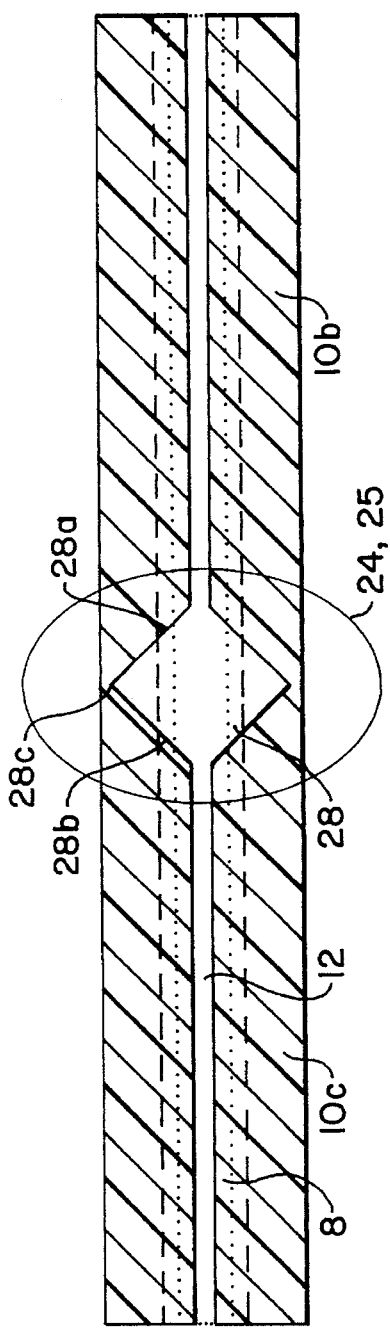
FIG. 4 illustrates a longitudinal cross-sectional exploded view of a hinging portion that joins displaceable portions of a sleeve of the present invention.

FIG. 4 illustrates an exploded longitudinal cross-sectional view of hinging portions 24, 25. In one preferred embodiment, hinging portions 24, 25 are formed by creating a triangular indentation 28 in the cylindrical sleeve 10. The base of the triangular indentation is the edge of the sleeve formed by the slit. The indentation can be formed during the manufacturing of the sleeve 10, or by deforming or cutting the material comprising sleeve 10.

The hypodermic needle assembly 2 remains in the safe position until a sufficiently large reactive axial force is created at upper rigid portion 10a of the sleeve 10, as shown in FIG. 3, to overcome the initial rigidity of Sleeve 10. The axial force on upper rigid portion 10a results from the needle administrator placing the tip end of the sleeve 10 in contact with the patient and applying force to the needle assembly 2. The axial force is the reaction force created by the patients body and is transmitted axially along the sleeve 10 and applied along the sides 28a of the triangular indentations 28 of the hinging portions 24, 25 as shown in FIG. 4. The force on side 28a creates a torque around an apex 28c of the triangular indentation 28. Additionally, the axial force applied to the apex 28c creates a torque around hinging portions 30, 31 and 26, 27. Because the plastic sleeve 10 does not substantially deform axially, the axial force is opposed by an equal axial force directed opposite to the applied axial force.

If the applied axial force exceeds a threshold axial force dictated by the geometry, dimensions and materials of the sleeve 10, the resulting torque causes the subportions of displaceable portions 10b and 10c of the sleeve 10 to be displaced away from the cannula 8 about hinging portions 26, 27 and 30, 31. Once the threshold axial force has been exceeded, very little additional force (if any) is necessarily applied to needle assembly 2 to cause further displacement of displaceable portions 10b and 10c. This is because relatively little compression of hinging portion 24, 25, other than that caused by the threshold axial force, results from the displacement of the subportions of displaceable portions 10b and 10c of the sleeve 10.

Figure 5:
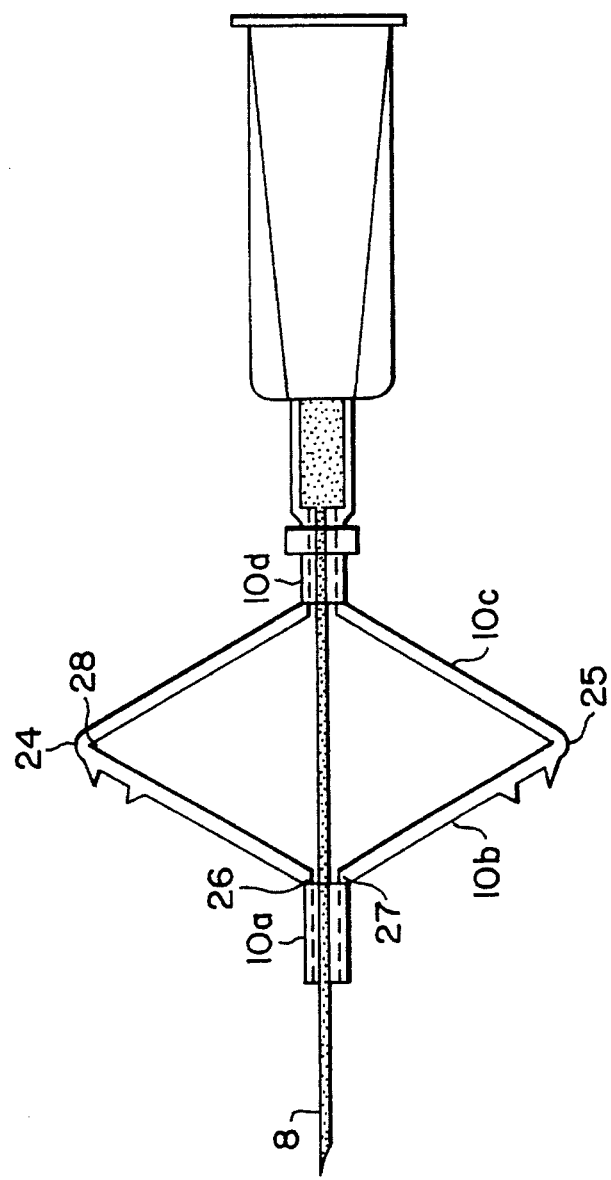
FIG. 5 illustrates the needle shield of the preferred embodiment of the present invention in an open position.

FIG. 5 illustrates sleeve 10 after an axial force exceeding the threshold has been applied. The displacement of the subportions of displaceable portions 10b and 10c of sleeve 10 allows the axial force to slidably move rigid upper portion 10a of the sleeve 10 axially down cannula 8, thereby facilitating insertion of the cannula 8 into the patient.

When the axial force is removed, such as when the cannula 8 is withdrawn from the patient, the compression force in hinging portion 28 creates a torque which causes the subportions of displaceable portions 10b and 10c of the sleeve 10 to return inward toward the cannula 8. This movement causes radially rigid upper portion 10a to slide axially toward the tip of cannula 8 until the sleeve 10 reverts to the safe position as shown in FIG. 2 (i.e. rigid portion 10a is at least coextensive with, if not extending beyond, the tip end of cannula 8). Because most hypodermic needles currently in use are disposed of after one injection, fatigue of hinging portion 24 should not be a factor in preventing a compressive force from restoring the sleeve 10 to the safe position. The shield of the current invention may be optimized for use with hypodermic needles that are used numerous times, such as for catheters, if a suitable material is chosen for hinging portions 24, 25.

Figure 6:
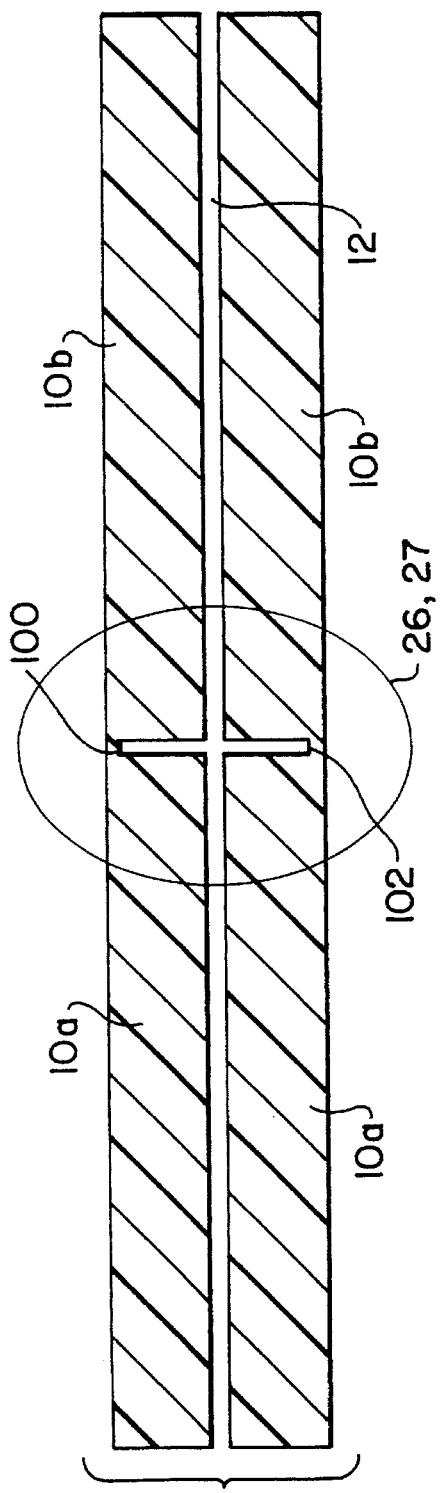
FIG. 6 illustrates a longitudinal cross-sectional exploded view of a hinging portion that joins a displaceable portion of the sleeve with a radially rigid portion of the sleeve.

As illustrated in FIG. 3, hinging portions 26, 27 and 30, 31 allow the subportions of displaceable portions 10b and 10c respectively to be displaced once the threshold force has been exceeded. Hinging portions 26, 27 may be implemented by forming slots 100, 102 in sleeve 10, as shown in FIG. 6. Hinging portions 30, 31 may be implemented in the same manner. Alternatively, if an increase in initial rigidity is desired, no slots need be formed and hinging portions 26, 27 and 30, 31 can be left to flex due to the inherent flexibility of the material from which sleeve 10 is made.

As shown in FIG. 5, in the preferred embodiment, hinging portions 26, 27 and 30, 31 exert equal forces to the displaceable portions 10b and 10c such that the subportions of displaceable portions 10b and 10c are substantially equally displaced from the cannula 8 upon application of an axial force that exceeds the threshold.

Figure 7:
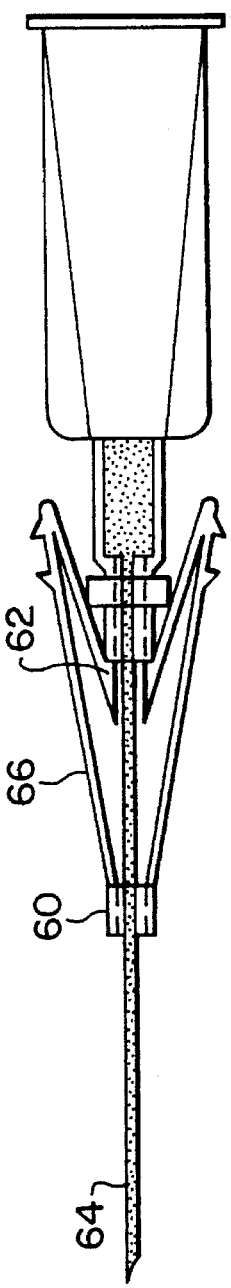
FIG. 7 illustrates an alternate embodiment of the sleeve of the present invention in an open position.

FIGS. 7 and 8 illustrate alternate embodiments of the hypodermic needle shield of the present invention. In the embodiment illustrated in FIG. 7, a hinging portion 60 towards the tip end of cannula 64 provides a greater force than a hinging portion 62 away from the tip of the cannula 64. The unequal forces cause a sleeve 66 to move into the position as shown in FIG. 7. Conversely, in the embodiment illustrated in FIG. 8, a hinging portion 68 towards the tip end of cannula 72 provides less force than a hinging portion 70 away from the tip end of cannula 72. The unequal forces cause sleeve 74 to move into the position as shown in FIG. 8. These embodiments may be preferable depending on the geometry of the surface to which the cannula 64 or 72 is to be applied.

If hinging portions 26, 27 (and 30, 31) are implemented by forming slots 100, 102 as illustrated in FIG. 6, the hinging portions may be manufactured to present unequal reactive forces by forming a slot of greater length for one hinging portion than another; the hinging portions provide a resistance to motion that is inversely proportional to the length of the slot. Alternatively, one hinging portion may include a slot while the other hinging portion does not include a slot. The hinging portion implemented with a slot will present less resistive force than the hinging portion not including a slot. Alternatively, hinging portions may be implemented by forming angled slots to influence the direction of displacement. In another embodiment, hinging portions may provide unequal forces by narrowing the sleeve 10 at one hinging portion more or less than at the other hinging portion. The hinging portion formed at the narrower part of the sleeve 10 will provide less resistive force than the other hinging portion. Finally, if a unitary sleeve is not employed, hinging portions may be manufactured to provide unequal forces by using different materials to form each hinging portion.

Those of skill in the art will recognize that there are many variables in the manufacturing process that can be altered to achieve different performance points. Rigidity and elasticity of the materials used to form the sleeve, the dimensions of the sleeve, the characteristics of the hinging portions, the number of subportions into which the displaceable portions are divided, etc. can all be varied to produce different threshold of displacement forces, different force versus displacement characteristics and the amount of compressive force available to return the sleeve to a safe position after withdrawal of the applied axial force from the shield. The preferred embodiment is disclosed as being unitary in nature, i.e. axially rigid portions 10a, 10d, displaceable portions 10b, 10c and hinging portions 24, 25, 26, 27, 30 and 31 are of integrated construction. It is conceivable, however, that some or all of the components of sleeve 10 can be separate and distinct. Of course, the hinging portions can be made out of more commonly known hinge mechanisms. So long as the above-contemplated variations of the preferred embodiment provide the desired characteristics: 1) an initial threshold force that must be exceeded for displacement of the sleeve can begin; 2) a force versus displacement curve that does not substantially exceed the threshold force over the desired range of displacement, and 3) a sufficient compressive force in the hinging portions of the sleeve to return the sleeve to the safe position upon removal of the force, these variations will fall within the intended scope of the present invention.

Figure 11A:
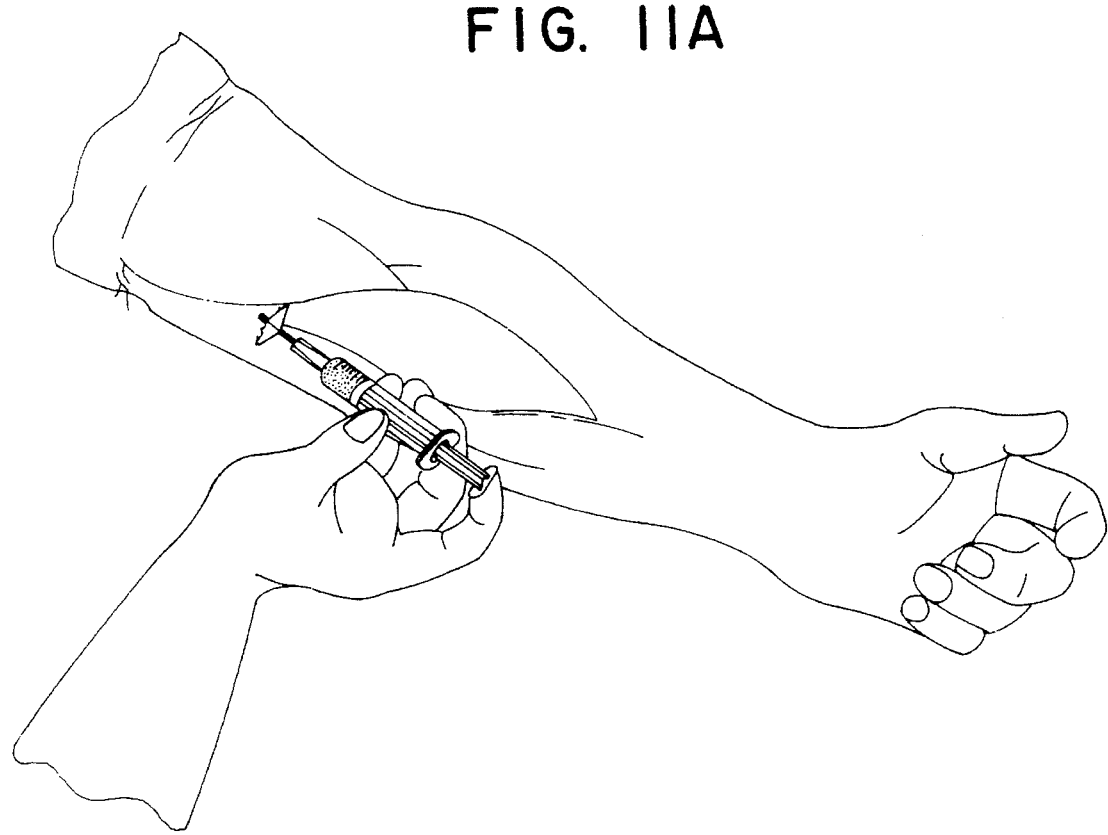
FIG. 11a illustrates a hypodermic needle in conjunction with the needle shield of the present invention being administered to a patient.
Figure 11B:
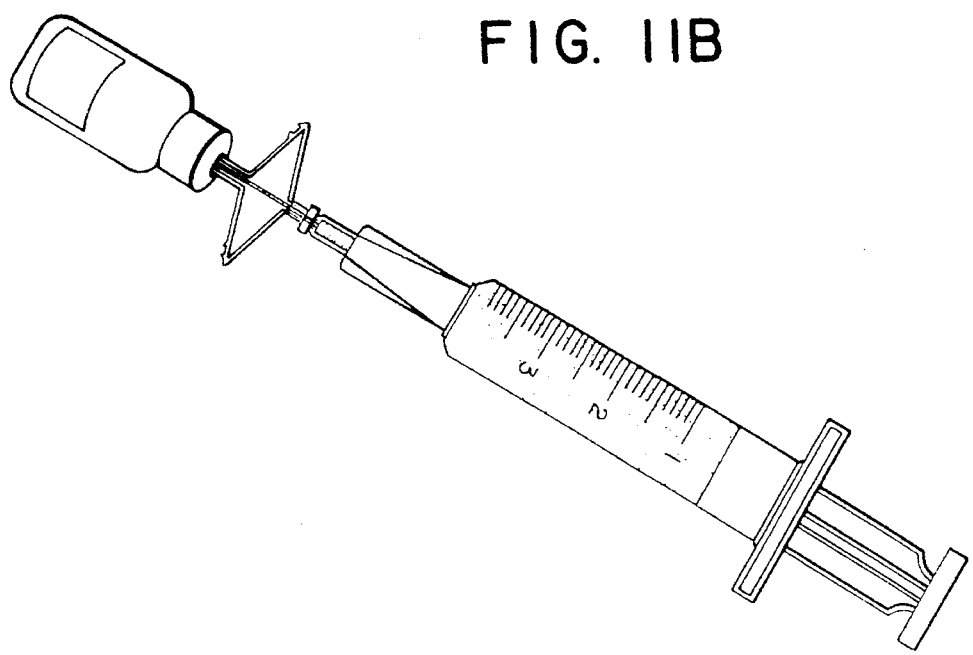
FIG. 11b illustrates a hypodermic needle and shield of the present invention as the needle is being filled from a vile.

The invention thus provides a hypodermic needle that will not be exposed unless a force is applied that exceeds some threshold. Unlike prior art devices, particularly those using springs, once the threshold force is exceeded, little additional force (if any) is required to cause further displacement of the shield and thus further exposure of the cannula 8. As shown in FIG. 11a, when a needle administrator applies the threshold force against a patient, the cannula 8 is inserted into the patient. The same is true when withdrawing drug from a vile as shown in FIG. 11b. When the needle administrator stops applying an axial force and withdraws the cannula 8 from the patient, it retracts into the sleeve 10. Once the cannula 8 is completely withdrawn from the patient, the cannula 8 is completely retracted into the sleeve 10 and the hypodermic needle shield is again in the safe position. Thus, the tip of the cannula 8 is exposed to the patient only during insertion and withdrawal of the needle, protecting needle administrators and others from accidental exposure to the tip of the cannula 8.

The needle shield of the present invention as shown in FIG. 2 may be locked in the safe position to further increase the amount of axial force required to cause accidental exposure of the cannula 8, as well as to make illicit use after disposal difficult. FIG. 9 illustrates the needle shield of the present invention in a locked position. As illustrated in FIG. 9, a collar 18 is disposed within a collar index 16 to further resist displacement of the displaceable portions 10b and 10c of the sleeve 10. As illustrated in FIG. 3, the displaceable portion 10b is preferably formed integrally with collar index 16. Collar index 16 is formed by borders which vary in diameter such that in the cross-sectional view of FIG. 3, the borders appear as four right triangles, 16a, 16b, 16c and 16d. The borders of collar index 16 are formed such that the diameter of the border defining the collar index represented by triangles 16a and 16c rises from a minimum value (i.e. the diameter of the sleeve) at a base point of the base of triangles 16a and 16c, toward the tip of the cannula 8, to a maximum value at a base point of the triangles 16a and 16c away from the tip of the cannula 8. Conversely, the diameter of the border forming collar index 16 represented by triangles 16b and 16d rises from a minimum value at a base point of triangles 16a and 16c away from the tip of the cannula 8 to a maximum value at a point of the base of the triangles 16a and 16c towards the tip of the cannula 8.

As shown in FIG. 1, in the safe position, the collar 18 is disposed at an end of the sleeve 10 away from the tip of the cannula 8, and forms a diameter that is preferably just greater than that of the sleeve. To lock the shield, the needle administrator slides the collar 18 axially along the sleeve 10 toward the collar index 16, a direction opposite to that typically associated with accidental exposure to a used cannula. The collar 18 stretches in diameter by the application of a distributed radial force created as the collar 18 is pushed along the increasing diameter of the border 16b, 16d. Thus, collar 18 slides axially along the sleeve 10 and stretches to traverse that portion of the collar index 16 represented by triangles 16b and 16d. Once in collar index 16, the collar resumes its normal diameter. Further axial movement of the collar 18 in either direction is prevented by the borders forming collar index 16.

In the locked position, if an axial force is applied to the sleeve 10 as illustrated in FIG. 3, the collar 18 prevents displacement of the displaceable portion 10b of the sleeve 10 by applying a force, directed radially inward toward the cannula 8, to the displaceable portion 10b of the sleeve 10. If the collar 18 is made of sufficiently rigid material, the collar 18 will restrict radial movement of the displaceable portion 10b of the sleeve 10, even for large axial forces applied to the sleeve 10. Of course, collar 18 must remain flexible enough to stretch over the border to engage index 16.

Figure 12A:
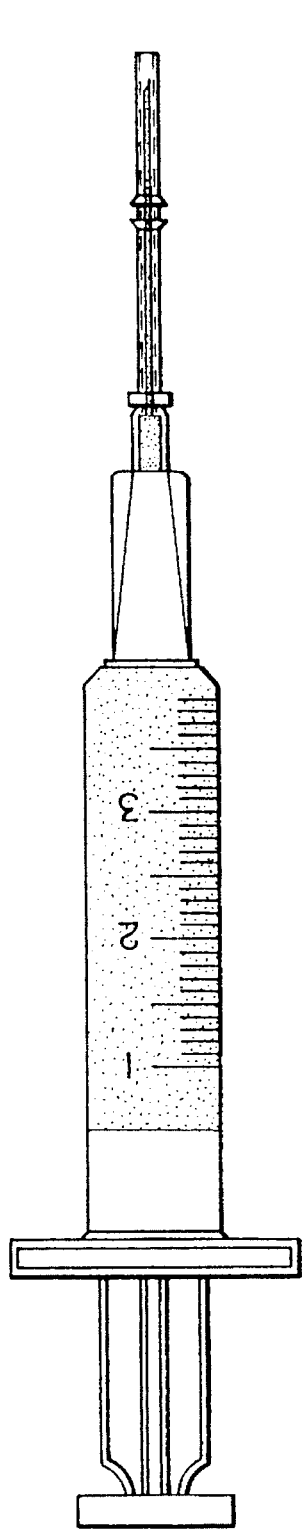
FIG. 12a illustrates the needle shield of the present invention in the safe position.
Figure 12B:
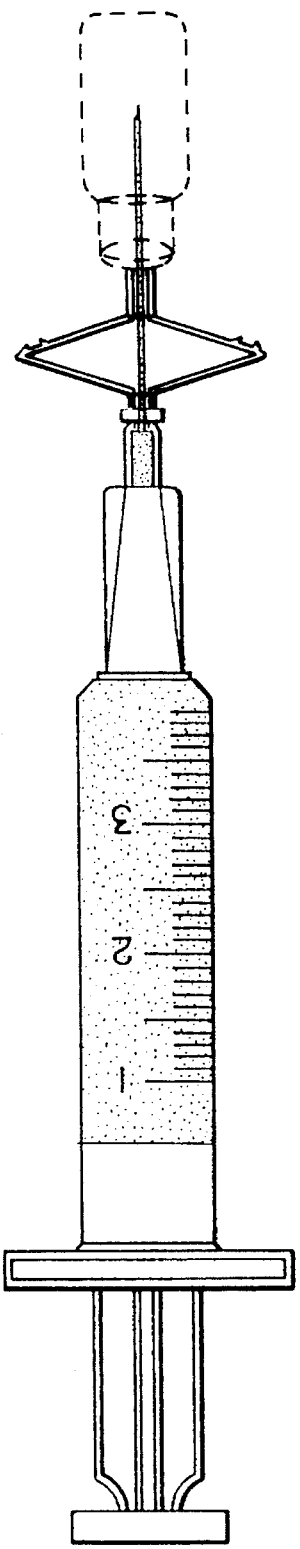
FIG. 12b illustrates the needle shield of the present invention in the exposed position under use.
Figure 12C:
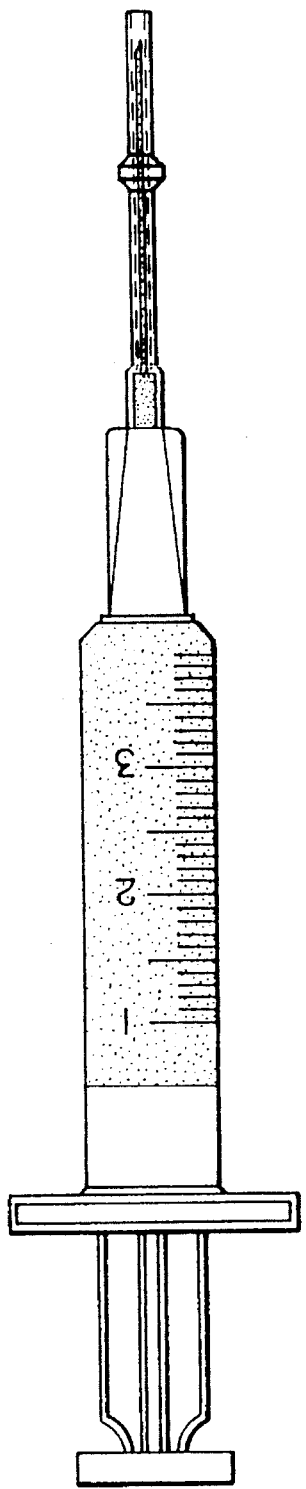
FIG. 12c illustrates the needle shield of the present invention in the safe and locked position.

While the needle administrator slides the collar 10, the cannula 8 remains completely housed within the sleeve 10 in the safe position. The operation of sliding the collar 18 towards the tip end of cannula 8 presents little risk of accidental exposure to the cannula 8. Should the needle administrator neglect to lock the shield in the safe position, accidental exposure to the cannula 8 is still prevented provided no axial force exceeding the threshold is applied. FIGS. 12*a*, 12*b* and 12*c* illustrate the shield of the present invention in the safe, the open and the locked positions respectively.

Figure 10A:
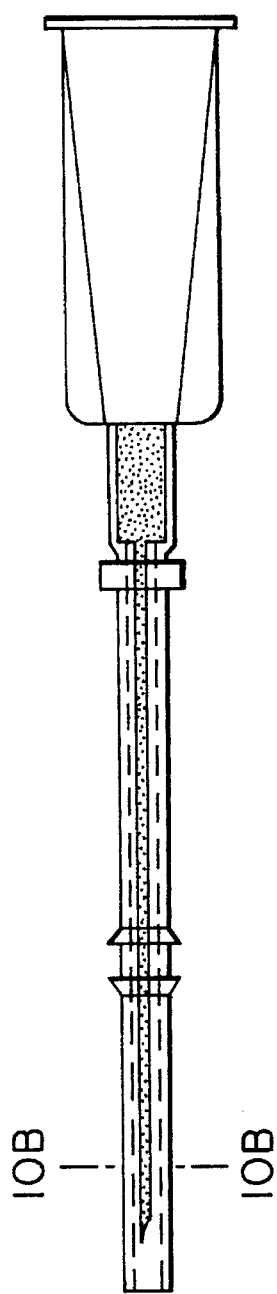
FIG. 10a illustrates channels that may be employed to divert excess blood from a cannula.
Figure 10B:
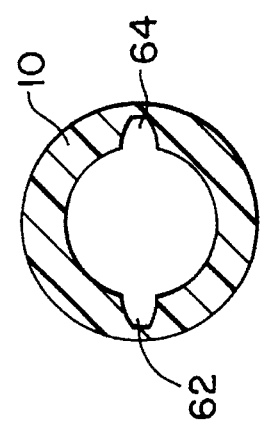
FIG. 10b illustrates the channels as a cross-sectional view through lines A—A.

To help prevent exposure to blood adhering to the cannula 8 as a result of insertion into a patient, one or more channels 62 and 64 may be formed in the sleeve 10 as shown in FIGS. 10*a* and 10*b*. As the anterior of the sleeve 10 moves along the cannula 8, excess blood will tend to gather in the channels 62 and 64 rather then be forced out through the end of sleeve 10.

In addition to the previously mentioned benefits, the needle shield of the present invention is easier to manufacture than prior art needle shields. Prior art needle shields typically contain many moving pieces. The hub 14 and the sleeve 10 of the present invention may be manufactured as a single unitary piece by a simple molding process, requiring only the recutting of an existing mold cavity. The cannula is inserted after the molding process and attached in the normal manner with, at most, a few minor modifications. The collar 18 and collar index 16 may also be assembled with the hub 14 and the sleeve 10 during the molding process. Thus, the shield of the present invention may be manufactured by a simple molding process that avoids expensive assembly procedures.

The present invention may be manufactured using other efficient techniques. For example, the needle shield of the present invention may also be coupled to existing hypodermic needle hubs by heat sealing or sonically melting the sleeve 10. Thus, an existing hypodermic needle manufacturer need not redesign a needle assembly to operate in conjunction with the shield of the present invention.

The invention has been described in conjunction with numerous preferred embodiments. Numerous alternatives, modifications, variations and uses will be apparent to those skilled in the art in light of the foregoing description. For example, the indentation of hinging portions 24, 25 may be formed of shapes other than a triangle such as a semi-circle. Instead of being formed by an indentation, hinging portions 24, 25 may be formed by joining subportions of displaceable portions 10*b* and 10*c* at an angle. Similarly, hinging portions 26, 27 and 30, 31 need not be implemented with slots. The shield of the present invention need not be formed as a unitary sleeve and many materials, other than those disclosed herein, will be recognized by those of skill in the art as suitable for constructing the sleeve.

What is claimed is:

1. A shield for a hypodermic needle assembly, said assembly comprising a cannula having a tip end, said cannula further having a base end coupled to a hub, said shield comprising:

a sleeve having an initial rigidity comprising:

(a) a bore for slidably receiving said cannula;

(b) a lower rigid portion coupled to said hub;

(c) an upper rigid portion at least coextensive with said tip end when said sleeve is in a safe position;

(d) at least two slits extending longitudinally between said upper and said lower rigid portions forming at least two displaceable portions, each comprising:

i) a first hinging portion located where said upper rigid portion and said each of said at least two displaceable portions interface;

ii) a second hinging portion located where said lower rigid portion and said each of said at least two displaceable portions interface; and iii) a third hinging portion located between said first and said second hinging portions;

wherein said sleeve possesses mechanical properties such that an axial force exceeding a threshold axial force must be applied to said upper rigid portion to overcome said initial rigidity, causing displacement of said at least two displaceable portions and slidably exposing said cannula thereby; and wherein said third hinging portion comprises a slot in the radially inner surface of said displaceable portion at the edges formed by said two or more slits so that said threshold axial force is not so great as to interfere with smooth administration of an injection, but is still greater than axial forces created unintentionally.

2. The apparatus of claim 1 wherein said sleeve further comprises at least one collar index, located circumferentially around two of said displaceable portions and formed by two borders, one of said borders having increasing diameter towards said index, said sleeve further comprising a collar through which said sleeve is disposed, said collar capable of stretching over said increasing diameter of said border to engage said index.

3. The apparatus of claim 1 wherein said sleeve further comprises at least two border means for defining at least one index means, said index means for engaging and locking a collar means, said collar means for preventing displacement of two of said displaceable portions.

* * * * *